United States Patent
Bhattacharyya

(10) Patent No.: US 7,457,454 B1
(45) Date of Patent: Nov. 25, 2008

(54) DETAILED GREY SCALE INSPECTION METHOD AND APPARATUS

(75) Inventor: Kaustuve Bhattacharyya, Schenectady, NY (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 584 days.

(21) Appl. No.: 10/267,016

(22) Filed: Oct. 8, 2002

(51) Int. Cl.
  *G06K 9/00* (2006.01)
  *G01R 31/26* (2006.01)
  *G01L 21/30* (2006.01)

(52) U.S. Cl. .............................. 382/149; 438/6; 216/60

(58) Field of Classification Search ......... 382/144–149; 438/16; 216/60
See application file for complete search history.

(56) References Cited

U.S. PATENT DOCUMENTS

| | | | | |
|---|---|---|---|---|
| 4,208,240 A | * | 6/1980 | Latos ........................... | 216/60 |
| 5,739,051 A | * | 4/1998 | Saito ........................... | 438/16 |
| 5,828,778 A | * | 10/1998 | Hagi et al. ................... | 382/145 |
| 5,978,501 A | * | 11/1999 | Badger et al. ............... | 382/144 |
| 6,117,348 A | * | 9/2000 | Peng et al. .................... | 216/60 |
| 6,175,646 B1 | * | 1/2001 | Schemmel et al. ........... | 382/149 |
| 6,849,470 B1 | * | 2/2005 | Eriguchi et al. ............... | 438/14 |
| 6,952,492 B2 | * | 10/2005 | Tanaka et al. ................ | 382/149 |
| 2003/0228050 A1 | * | 12/2003 | Geshel et al. ............... | 382/149 |
| 2004/0028267 A1 | * | 2/2004 | Shoham et al. | |

* cited by examiner

*Primary Examiner*—Jingge Wu
*Assistant Examiner*—Kathleen S Yuan
(74) *Attorney, Agent, or Firm*—Smyrski Law Group, A P.C.

(57) ABSTRACT

A method for inspecting semiconductor wafers and the like is presented. The method comprises initially determining a baseline greyscale difference, such as a greyscale plot or greyscale visual representation, for at least one baseline semiconductor wafer subjected to a process. The baseline greyscale difference represents a numerical difference between composite preprocessing and postprocessing greyscale representations of all pixels on the baseline semiconductor wafer. The method further comprises determining a preprocess greyscale representation for one wafer in the semiconductor wafer set and subjecting the one wafer in the semiconductor wafer set to the process, determining a postprocess greyscale representation of the one wafer in the semiconductor wafer set, and determining a difference for the one wafer in the semiconductor set. The difference represents any disparity between preprocess and postprocess greyscale representations of the one wafer in the semiconductor set. The method then compares the difference to the baseline greyscale difference.

25 Claims, 4 Drawing Sheets

DETAILED GREY SCALE INSPECTION METHOD AND APPARATUS

BACKGROUND OF THE INVENTION

1. Field of the Invention

The present invention relates generally to the field of electro-optical inspection systems, and more particularly to grey scale wafer inspection to detect defects on processed semiconductor wafers and the like.

2. Description of the Related Art

Integrated circuits are produced using photolithographic processes on specimens, such as silicon wafers. These processes can employ photomasks or reticles and a light source to project a circuit image onto the silicon wafer. The presence of surface defects on the wafer, particularly after undergoing the photolithographic process, is highly undesirable and adversely affect the resulting circuits. Defects can result from, but not limited to, a portion of the pattern being absent from an area where it is intended to be present, a portion of the pattern being present in an area where it is not intended to be, chemical stains or residues from the photomask manufacturing processes which cause an unintended localized modification of the light transmission property of the photomask, particulate contaminates such as dust, resist flakes, skin flakes, erosion of the photolithographic pattern due to electrostatic discharge, artifacts in the photomask substrate such as pits, scratches, and striations, and localized light transmission errors in the substrate or pattern layer. Since it is inevitable that defects will occur, these defects are preferably located and repaired prior to use.

Methods and apparatus for detecting defects have been generally available. For example, inspection systems and methods utilizing laser light are available to scan the surface of substrates such as photomasks, reticles and wafers. These laser inspection systems and methods generally include a laser source for emitting a laser beam, optics for focusing the laser beam to a scanning spot on the surface of the substrate, a stage for providing translational travel, collection optics for collecting either transmitted and/or reflected light, detectors for detecting either the transmitted and/or reflected light, sampling the signals at precise intervals and using this information to construct a virtual image of the substrate being inspected.

Although such systems work well under many conditions, ongoing work in the area seeks to improve existing designs to enable higher degrees of sensitivity, increase the ability to classify and quantify defects, and to allow faster scanning speeds and higher throughput. As the complexity of integrated circuits has increased, the demands on the inspection of the integrated circuits have also increased. Both the need for resolving smaller defects and for inspecting larger areas have resulted in greater magnification requirements and greater speed requirements.

During the manufacture of wafers having patterns etched thereon, automated inspection of the wafer is performed to ensure freedom from the aforementioned defects. Various methods for the inspection of patterned masks, reticles, or the wafer surface are currently available. Many of the available processes, such as ion implant, oxidation, CVD (chemical vapor deposition), etching, and so forth cause a difference in the optical appearance of the wafer before and after such a process occurs. Changes in the appearance of a wafer before and after a process step can be optically detected by measuring the composite greyscale difference of the whole wafer at preprocessing time and subsequently at postprocessing time. This method can be utilized to verify complete or partial completion of a process. Previous systems have used single pixel grey scale difference comparisons between preprocessed and postprocessed wafers to determine the defects on the wafer and the quality of the process employed. These systems generally made a pixel by pixel comparison between the preprocessed and postprocessed surface representations, and generally required a calibration or matching process before making such a comparison. Single pixel greyscale difference measurements before and after processing are generally not sensitive enough to detect the difference of the optical appearance change.

Other previous systems used reflectivity measurements to determine wafer defects and the quality of the process. Use of reflectivity measurements can result in problems due to process variation induced noise. Gross defects can be detected on wafers using reflectivity measurements, but inspection sensitivity and ultimate results can be compromised by intrinsic process variation. In this instance, process variation may be interpreted as noise by the system, and requires desensitizing the inspection to prevent false positives, or false indications that a defect exists. Use of reflectivity measurements places entire classes of defects below the detection threshold of the inspection system, and thus the slight change in greyscale value can go undetected.

Based on the foregoing, it would be beneficial to provide a system which did not include certain drawbacks associated with previous wafer inspection systems.

SUMMARY OF THE INVENTION

According to one aspect of the present invention, there is provided a method for inspecting a semiconductor wafer set. The method comprises initially determining a baseline greyscale difference representation for at least one baseline semiconductor wafer subjected to a process, wherein the baseline greyscale difference representation represents a difference between a baseline preprocess greyscale representation and a baseline postprocess greyscale representation. The method further comprises determining a preprocess greyscale representation for one wafer in the semiconductor wafer set, subjecting the one wafer in the semiconductor wafer set to the process, determining a postprocess greyscale representation of the one wafer in the semiconductor wafer set, and determining a difference for the one wafer in the semiconductor set. The difference represents any disparity between preprocess and post process greyscale representations of the one wafer in the semiconductor set. The method then compares the difference to the baseline greyscale difference representation.

According to a second aspect of the invention, there is provided a method for inspecting a semiconductor wafer, comprising determining a preprocess greyscale representation for the wafer, subjecting the wafer to a process, determining a postprocess greyscale representation for the wafer, and determining a difference for the wafer, wherein the difference represents any disparity between preprocess and post process greyscale representations of the wafer.

According to a third aspect of the invention, there is provided a method for inspecting a specimen, comprising determining a preprocess greyscale representation of the wafer, computing a preprocess numeric greyscale value representing the preprocess greyscale representation of the wafer, subjecting the wafer to a process, determining a postprocess greyscale representation of the wafer, computing a postprocess numeric greyscale value representing the postprocess greyscale representation of the wafer, and comparing the preprocess numeric greyscale value to the postprocess greyscale value.

These and other advantages of all aspects of the present invention will become apparent to those skilled in the art after having read the following detailed disclosure of the preferred embodiments illustrated in the following drawings.

DESCRIPTION OF THE DRAWINGS

The present invention is illustrated by way of example, and not by way of limitation, in the figures of the accompanying drawings in which.

DETAILED DESCRIPTION OF THE INVENTION

The present system and method may be implemented on a variety of inspection systems. The following represents a generalized representation of a system employing the current design.

Figure 1:
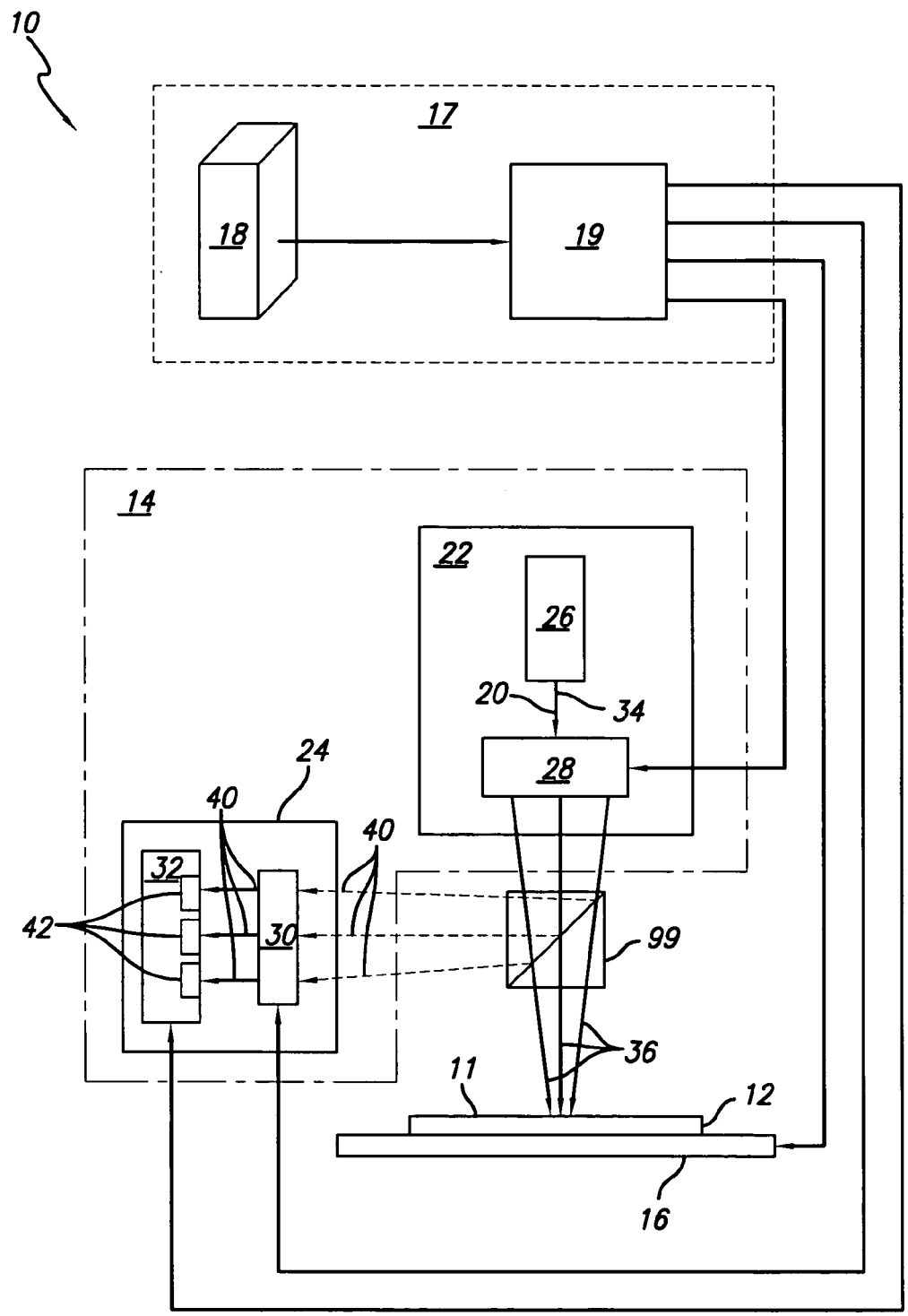
FIG. 1 is a simplified block diagram of an optical inspection system in accordance with one aspect of the present invention.

FIG. 1 is a simplified block diagram of an optical inspection system 10, in accordance with one aspect of the present invention. The optical inspection system 10 is arranged for inspecting a surface 11 of a substrate 12. The dimensions of various components are exaggerated to better illustrate the optical components of this embodiment. As shown, the optical inspection system 10 includes an optical assembly 14, a stage 16, and a control system 17. The optical assembly 14 generally includes at least a first optical arrangement 22 and possibly a second optical arrangement 24. In general terms, the first optical arrangement 22 generates two or more beams incident on the substrate or wafer surface, and the second optical arrangement 24 detects two or more beams emanating from the sample as a result of the two or more incident beams. The first and second optical arrangement may be arranged in suitable manner in relation to each other. For example, the second optical arrangement 24 and the first optical arrangement 22 may both be arranged over the substrate surface 11 so that reflected beams resulting from incident beams generated by the first optical arrangement 22 may be detected by the second optical arrangement 24.

In the illustrated system, the first optical arrangement 22 is arranged for generating a plurality of scanning spots (not shown) along an optical axis 20. As should be appreciated, the scanning spots are used to scan the surface 11 of the substrate 12. On the other hand, the second optical arrangement 24 is arranged for collecting transmitted and/or reflected light that is produced by moving the scanning spots across the surface 11 of the substrate 12.

The first optical arrangement 22 includes at least a light source 26 for emitting a light beam 34 and a first set of optical elements 28. The first set of optical elements 28 may be arranged to provide one or more optical capabilities including, but not limited to, separating the light beam 34 into a plurality of incident light beams 36, directing the plurality of incident light beams 36 through a beamsplitter or beamsplitter arrangement 99 to intersect with the surface 11 of the substrate 12. The result is focusing the plurality of incident light beams 36 to a plurality of scanning spots (not shown in FIG. 1) on the surface 11 of the substrate 12. The amount of first beams produced generally corresponds to the desired inspection speed. In one aspect, the optical elements may be arranged to separate the beam 34 into three incident light beams 36. By triplicating the beam, a wider scan is produced and therefore the resulting inspection speed is about three times faster than the speed produced for a non-triplicated single beam. Although only three light beams are shown, it should be understood that the number of separated light beams may vary according to the specific needs of each optical inspection system. For example, two beams may be used or four or more beams may be used. It should be noted, however, that the complexity of the optic elements is directly proportional to the number of beams produced.

Furthermore, the second optical arrangement 24 includes at least a second set of optical elements 30 and a light detecting arrangement 32. The second set of optical elements 30 receive light energy reflected from the wafer surface in the path of a plurality of collected light beams 40, which are formed after the plurality of incident light beams 36 intersect with the surface 11 of the wafer or substrate 12. The beamsplitter 99 redirects the collected light beams 40 to the set of optical elements 30. The plurality of collected light beams 40 may result from reflected light that is reflected off the surface 11 of the substrate 12. The second set of optical elements 30 are adapted for collecting the plurality of collected light beams 40 and for focusing the collected light beams 40 on the light detecting arrangement 32. The light detecting arrangement 32 is arranged for detecting the light intensity of the collected light beams 40, and more particularly for detecting changes in the intensity of light caused by the intersection of the plurality of incident light beams with the substrate. The light detecting arrangement 32 generally includes individual light detectors 42 that correspond to each of the second light beams 40. Furthermore, each of the detectors 42 is arranged for detecting the light intensity and for generating signals based on the detected light.

With regards to the stage 16, the stage 16 is arranged for moving the substrate 12 within a single plane (e.g., x & y directions) and relative to the optical axis 20, so that all or any selected part of the substrate surface 11 may be inspected by the scanning spots. In most embodiments, the stage 16 is arranged to move in a serpentine fashion. With regards to the control system 17, the control system 17 generally includes a control computer 18 and an electronic subsystem 19. Although not shown, the control system 17 may also include a keyboard for accepting operator inputs, a monitor for providing visual displays of the inspected substrate (e.g., defects), a database for storing reference information, and a recorder for recording the location of defects. As shown, the control computer 18 is coupled to the electronic subsystem 19 and the electronic subsystem 19 is coupled to various components of the optical inspection system 10, and more particularly to the stage 16 and the optical assembly 14 including the first optical arrangement 22 and the second optical arrangement 24. The control computer 18 may be arranged to act as an operator console and master controller of the system. That is, all system interfaces with an operator and the user's facilities may be made through the control computer 18. Commands may be issued to and status may be monitored from all other subsystems so as to facilitate completion of operator assigned tasks.

On the other hand, the electronics subsystem 19 may also be configured to interpret and execute the commands issued by control computer 18. The configuration may include capabilities for, but not limited to, digitizing the input from detectors, compensating these readings for variations in the incident light intensity, constructing a virtual image of the substrate surface based on the detected signals, detecting defects in the image and transferring the defect data to the control computer 18, accumulating the output of the interferometers used to track the stage 16, providing the drive for linear motors that move the stage 16 or components of the optical assembly 14, and monitoring sensors which indicate status. Control systems and stages are well know in the art and for the sake of brevity will not be discussed in greater detail. By way of example, a representative stage, as well as a representative controller may be found in U.S. Pat. No. 5,563,702. It should be understood, however, that this is not a limitation and that other suitable stages and control systems may be used.

One specific system that may employ the current design is presented below. A block diagram of an automatic optical inspection system is shown at 10. The system is capable of inspecting substrates, including reticles, photomasks, and semiconductor wafers.

In most of the defect detection operations a comparison is made between two images. By way of example, the comparison may be implemented by the electronic subsystem 19 of FIG. 1. Broadly speaking, the detectors 42 generate scan signals, which are based on the measured light intensity, and send the scan signals to the electronic subsystem 19. The electronic subsystem 19, after receiving the scan signals, correspondingly compares the scan signals with reference signals, which are either stored in a database or determined in a current or previous scan.

Figure 2:
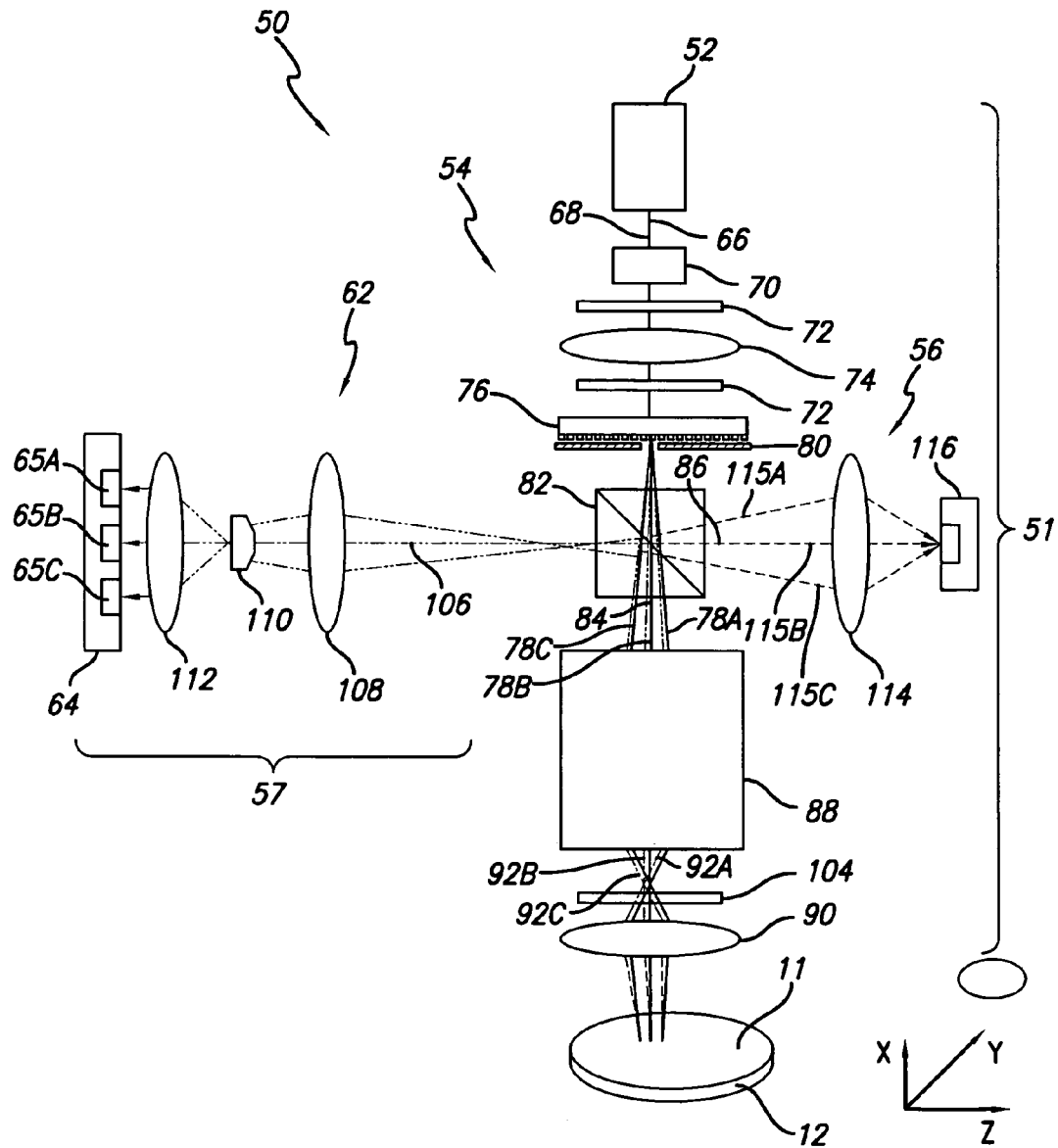
FIG. 2 is a detailed block diagram of an optical inspection system for inspecting a surface of a semiconductor wafer.

FIG. 2 is a detailed block diagram of an optical assembly 50 for inspecting the surface 11 of the substrate 12, in accordance with one available aspect of the present invention. By way of example, the optical assembly 50 may be the optical assembly 14 as described with respect to FIG. 1. The optical assembly 50 generally includes a first optical arrangement 51 which may respectively correspond to the first optical arrangement 22 of FIG. 1. As shown, the first optical arrangement 51 includes at least a light source 52, inspection optics 54, and reference optics 56, while the second optical arrangement 57 includes at least transmitted light optics 58, transmitted light detectors 60, reflected light optics 62, and reflected light detectors 64.

The light source 52 is arranged for emitting a light beam 66 along a first path 68. The light beam 66 emitted by the light source 52, first passes through an acousto optic device 70, which is arranged for deflecting and focusing the light beam. Although not shown, the acousto optic device 70 may include a pair of acousto-optic elements, which may be an acousto-optic prescanner and an acousto-optic scanner. These two elements deflect the light beam in the Y-direction and focus it in the Z-direction. By way of example, most acousto-optic devices operate by sending an RF signal to quartz or a crystal such as $TeO_2$. The signal causes a sound wave to travel through the crystal. Because of the traveling sound wave, the crystal becomes asymmetric, which causes the index of refraction to change throughout the crystal. This change causes incident beams to form a focused traveling spot which is deflected in an oscillatory fashion.

When the light beam 66 emerges from the acousto-optic device 70, it then passes through a pair of quarter wave plates 72 and a relay lens 74. The relay lens 74 is arranged to collimate the light beam 66. The collimated light beam 66 then continues on its path until it reaches a diffraction grating 76. The diffraction grating 76 is arranged for flaring out the light beam 66, and more particularly for separating the light beam 66 into three distinct beams, which are designated 78A, 78B and 78C. In other words, each of the beams are spatially distinguishable from one another (i.e., spatially distinct). In most cases, the spatially distinct beams 78A, 78B and 78C are also arranged to be equally spaced apart and have substantially equal light intensities.

Upon leaving the diffraction grating 76, the three beams 78A, 78B and 78C pass through an aperture 80 and then continue along path 68 until they reach a beam splitter cube 82. The beam splitter cube 82 (working with the quarter wave plates 72) is arranged to divide the beams into paths 84 and 86. Path 84 is used to distribute a first light portion of the beams to the substrate 12 and path 86 is used to distribute a second light portion of the beams to the reference optics 56. In most embodiments, most of the light is distributed to the substrate 12 along path 84 and a small percentage of the light is distributed to the reference optics 56 along path 86. It should be understood, however, that the percentage ratios may vary according to the specific design of each optical inspection system. In brief, the reference optics 56 include a reference collection lens 114 and a reference detector 116. The reference collection lens 114 is arranged to collect and direct the second portion of the beams, now designated 115A-C, on the reference detector 116. As should be appreciated, the reference detector 116 is arranged to measure the intensity of the light. Although not shown in FIG. 2, the reference detector 116 is generally coupled to an electronic subsystem such as the electronic subsystem 19 of FIG. 1 such that the data collected by the detector can be transferred to the control system for analysis. Reference optics are generally well known in the art.

The three beams 78A, 78B and 78C continuing along path 84 are received by a telescope 88. Although not shown, inside the telescope 88 there are a several lens elements that redirect and expand the light. In one embodiment, the telescope is part of a telescope system that includes a plurality of telescopes rotating on a turret. For example, three telescopes may be used. The purpose of these telescopes is to vary the size of the scanning spot on the substrate and thereby allow selection of the minimum detectable defect size. More particularly, each of the telescopes generally represents a different pixel size. As such, one telescope may generate a larger spot size making the inspection faster and less sensitive (e.g., low resolution), while another telescope may generate a smaller spot size making inspection slower and more sensitive (e.g., high resolution).

From the telescope 88, the beams 78A, 78B and 78C pass through an objective lens 90, which is arranged for focusing the beams 78A, 78B and 78C onto the surface 11 of the substrate 12. As the beams 78A-C intersect the surface 11 of the substrate 12 reflected light beams 92A, 92B, and 92C may be generated. The reflected light beams 92A, 92B, and 92C reflect off the surface 11 of the substrate 12. By way of example, the reflected light beams 92A, 92B, and 92C may reflect off of an opaque surfaces of the substrate. The reflected light beams 92 are collected by the reflected light optics 62.

With regards to the reflected light optics 62, the reflected light beams 92A, 92B, and 92C after reflecting off of the substrate 12 are collected by the objective lens 90, which then directs the beams 92A-C towards the telescope 88. Before reaching the telescope 88, the beams 92A-C also pass through a quarter wave plate 104. In general terms, the objective lens 90 and the telescope 88 manipulate the collected beams in a manner that is optically reverse in relation to how the incident beams are manipulated. That is, the objective lens 90 re-collimates the beams 92A, 92B, and 92C, and the telescope 88 reduces their size. When the beams 92A, 92B, and 92C leave the telescope 88, they continue along path 84 (backwards) until they reach the beam splitter cube 82. The beam splitter 82 is arranged to work with the quarter wave-plate 104 to direct the beams 92A, 92B, and 92C onto a path 106.

The beams 92A, 92B, and 92C continuing on path 106 are then collected by a first reflected lens 108, which focuses each of the beams 92A, 92B, and 92C onto a reflected prism 110, which includes a facet for each of the reflected light beams 92A-C. The reflected prism 110 is arranged for repositioning and bending the reflected light beams 92A, 92B, 92C. The reflected prism 110 is used to separate the beams so that they each fall on a single detector in the reflected light detector arrangement 64. As shown, the reflected light detector arrangement 64 includes three individually distinct detectors 65A-C, and more particularly a first reflected detector 65A, a second reflected detector 65B, and a third reflected detector 65C. Of course, each detector may be packaged separately or together. When the beams 92A-C leave the prism 110, they pass through a second reflected lens 112, which individually focuses each of the separated beams 92A, 92B, 92C onto one of these detectors 65A-C. For example, beam 92A is focused onto reflected detector 65A; beam 92B is focused onto reflected detector 65B; and beam 92C is focused onto reflected detector 65C. As should be appreciated, each of the reflected detectors 65A, 65B, or 65C is arranged for measuring the intensity of the reflected light.

For use with the present invention, it is assumed that only a reflected light inspection mode will be employed. With regards to reflected light inspection mode, reflected light inspection can be performed on transparent or opaque substrates that contain image information in the form of chromium, developed photoresist or other features. Light reflected by the substrate 12 passes backwards along the same optical path as the inspection optics 54 but is then diverted by a polarizing beam splitter 82 into detectors 65A-C. More particularly, the first reflected lens 108, the prism 110 and the second reflected lens 112 project the light from the diverted light beams 92A-C onto the detectors 65A-C. Reflected light inspection may be used to detect contamination on top of opaque substrate surfaces.

Further details of the system of FIGS. 1 and 2 wherein the present invention may be employed may be found in U.S. patent application Ser. No. 09/636,124, filed Aug. 10, 2000, and U.S. patent application Ser. No. 09/636,129, filed Aug. 10, 2000, both assigned to the assignee of the present invention, the entirety of which are incorporated herein by reference. As may be appreciated to those skilled in the art, other systems and designs may be used to practice the present invention.

Figure 3:
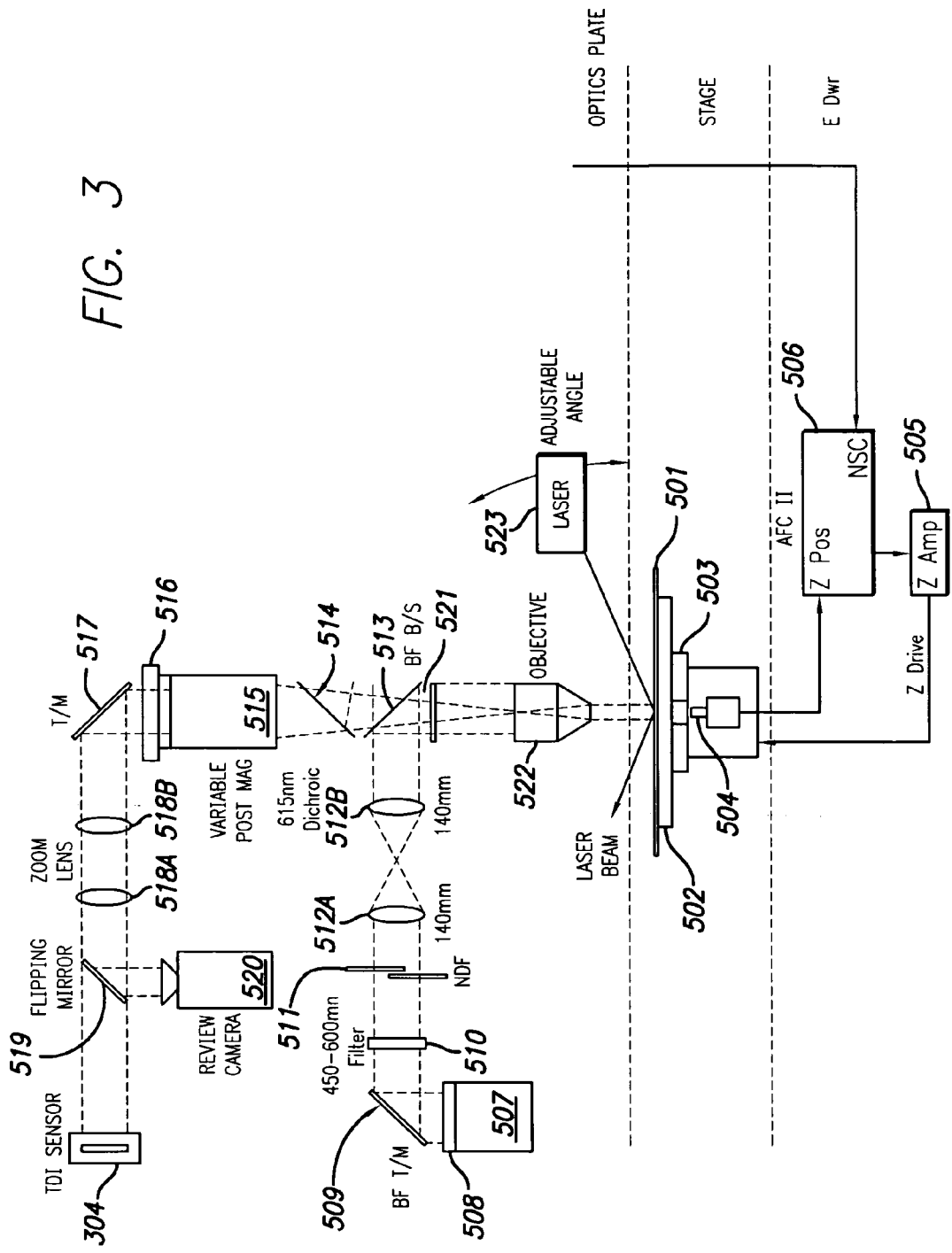
FIG. 3 illustrates a further system capable of employing the current invention.

FIG. 3 illustrates another inspection system that may also employ the current invention. Wafer 501 lies on chuck 502 which interacts with theta brake 503 and ECS head 504. A feedback loop between the drive unit 506, drive amplifier 505, and the ECS head 504 provides a uniform movement of the components and wafer 501 based on a control signal received from the optics plate. The wafer is illuminated in brightfield using brightfield illuminator 507 having illuminator lens arrangement 508, brightfield turning mirror 509, 450-600 nm filter 510, ND (neutral density) filter 511, and dual 140 mm lens arrangement 512a and 512b. Broadband brightfield light passes from dual 140 mm lens arrangement 512a and 512b to brightfield beamsplitter 513, which passes some light and reflects other light through turret turning mirror 514. Light thereupon passes through objective 515, which contains a condensing lens to focus the light, and thereupon onto wafer 501. Light is reflected from wafer 501 back through objective 515, turret turning mirror 514, brightfield/darkfield beamsplitter arrangement 513, and through 615 nm dichroic mirror 514, variable post mag 515, fourier filter 516, upper turning mirror 517, zoom lens arrangement 518a and 518b, and flipping mirror 519 to review camera 520 and sensor 304.

Under darkfield illumination, adjustable angle laser arrangement 521 directs laser beams over the wafer at a variable angle, where refraction from the wafer passes through objective 515, turret turning mirror 514, brightfield/darkfield beamsplitter arrangement 513, 615 nm dichroic mirror 514, variable post mag 515, fourier filter 516, upper turning mirror 517, zoom lens arrangement 518a and 518b, and flipping mirror 519 to review camera 520 and sensor 304. Using this structure, greyscale representations of the wafer may be collected.

The functionality critical to the present invention is that of providing light intensity to the sensors such that the optical appearance of any pattern or feature on the wafer or specimen can be processed. Other mechanizations besides those presented in FIGS. 1 through 3 may be employed with similarly beneficial results. The invention can be implemented using virtually any inspection machine, and the system may employ generic digital still picture cameras or image capturing devices to capture greyscale images of the wafer or wafers.

Greyscale Inspection and Comparison

Operation of the system is as follows. Prior to processing, it is desirable to establish a baseline pre- and post-processing greyscale comparison, wherein a successful process yields a satisfactory before processing greyscale representation of a wafer and a satisfactory after processing greyscale representation of the wafer. As used herein and as described in further detail hereinbelow, the term "greyscale representation" means a composite greyscale numeric value of all the pixels on the wafer and not just a single pixel value. This composite greyscale numeric value can provide enhanced sensitivity for a minute change in appearance of the wafer as a result of subjecting the wafer to a process.

The preprocessing and postprocessing set of scans constitutes a baseline comparison or calibration comparison that can be scanned in the entirety and compared. In other words, the entire greyscale representation of the pre-processed wafer is assigned a greyscale value, such as a value between 1 and X, where X may take any quantity including but not limited to 256, and the entire greyscale representation of the post-processed wafer is assigned a greyscale value in the same range, such as a value between 1 and X, where X may take any quantity including but not limited to 256. The two greyscale values are subtracted, and the resultant difference and the pre- and post-processing greyscale values can be saved to a database, including a reference to the type of process performed. Any one or a combination of the difference, the pre processing greyscale value, and the post processing greyscale value may be retained as a baseline comparison set.

Once the baseline comparison set has been established, the system can inspect pre-processed and post-processed subject wafers. The system inspects the entire semiconductor wafer before a specific process, such as ion implanting. The inspection includes a gray scale value collection of all of the pixels over the entire surface of the wafer. This may be done for any single wafer or group of wafers, including performing a scan on a first wafer and a last wafer to be processed at a later time. Each and every wafer in the lot may then be processed, in this example subjected to ion implanting. After processing, the wafers are again loaded individually into the system and the same wafer or wafers are inspected as had been inspected prior to processing, and the system collects grey scale values for the specific processed wafers. For example, if only one wafer was inspected before processing, the same is inspected after processing. Similarly, if the first and last wafers processed were inspected before processing, those two are inspected after processing and grey scale values collected. More or fewer may be inspected before and after processing. The system, typically using a processor or computing device, then compares the pre- and post-process grey scale values against one another for each wafer in the selected group. The system may then compare the result of the pre- and post-processed greyscale representations against the baseline comparison set. An acceptable boundary range, known as a difference boundary range, may be established, and a value outside this difference boundary range may be considered unacceptable. Additionally, boundaries for pre and post processed wafers may be established independent of one another and independent of the difference boundary range.

As an example, a system may operate with a 256 bit greyscale range, with 0 representing black and 255 representing white. The process evaluated may be ion implant, and a pre-processing greyscale value may be 128 for all pixels over the entire pre-processed wafer. A post-processing greyscale value may be 108, such that the difference therebetween is 20. Based on this, a value of 5 may be considered the boundary range, such that a value greater than 25 or less than 15 would be considered unacceptable. A boundary range of 10 for the pre-processed and 12 for the post-processed wafer, for example, may be established such that preprocessed greyscale values greater than 138 or less than 118 would be flagged, while post-processed values greater than 120 or less than 96 would be flagged. Depending on circumstances, these values may be employed for further investigation. For example, if the difference found is within acceptable boundaries, for example a difference value of 24 in the foregoing example, the system may nevertheless flag the wafer if either or both of the pre- or post-processed representations are outside their respective ranges. In this example, if the difference is 24, and the pre-processed value is 119 (within acceptable range for this example) but the post processed value is 95 (outside the acceptable range), the wafer may nevertheless be considered for subsequent inspection and/or flagged as bad.

If the first and last wafers in the process have been inspected pre-processing, they are also inspected post-processing, the greyscale difference for each wafer computed, and these differences each compared against the baseline comparison set, including possible comparison of the pre- and post-processing greyscale values. If the difference in the greyscale values is within range, the process is assessed to have been completed properly. If the difference is outside the accepted range, the process is considered incomplete or overdone. Overdone is generally considered an over application of a process, such as double implanting in an ion implantation situation.

In a situation where no baseline information is available, as well as any situation wherein one cannot readily determine when the process has begun or completed, or where one cannot assess the percentage a process has completed, additional steps may be employed. In such instances, the system may determine greyscale curves indicating the greyscale values expected at different steps in the process in order to accurately assess process completion, or alternately to assess performance of the processing. For example, if a typical process takes twenty minutes to complete, and a greyscale curve at 10 minutes indicates the wafer should exhibit a 75 percent difference from the original greyscale values, a wafer showing only a 20 percent difference may demonstrate a breakdown of the process. This greyscale curve may be created from prior knowledge or observation of points during the particular process for an ideal wafer.

In this aspect of the invention, the system may inspect multiple wafers prior to processing and collect multiple greyscale values, including values corresponding to each inspected wafer, for all wafers in the desired group. Once pre-processing greyscale representations of wafers in the desired group have been collected, the system or operator may process one wafer for a particular amount of time. The wafer is then inspected and a greyscale value determined. The greyscale value from the greyscale curve associated with that amount of time, or quantity of processing, should correspond to the greyscale value determined by inspection. Higher or lower greyscale values may indicate an error in processing, error in the wafer, or some other problem.

Multiple steps in a long process may employ the invention, wherein baseline greyscale values and/or differences at the specific points of a large or lengthy process are located and compared. For example, a large process may be stopped at multiple points to determine the quality of the processing to that particular point. Also, multiple verifications may be performed as the wafer progresses through the fabrication process.

Figure 4:
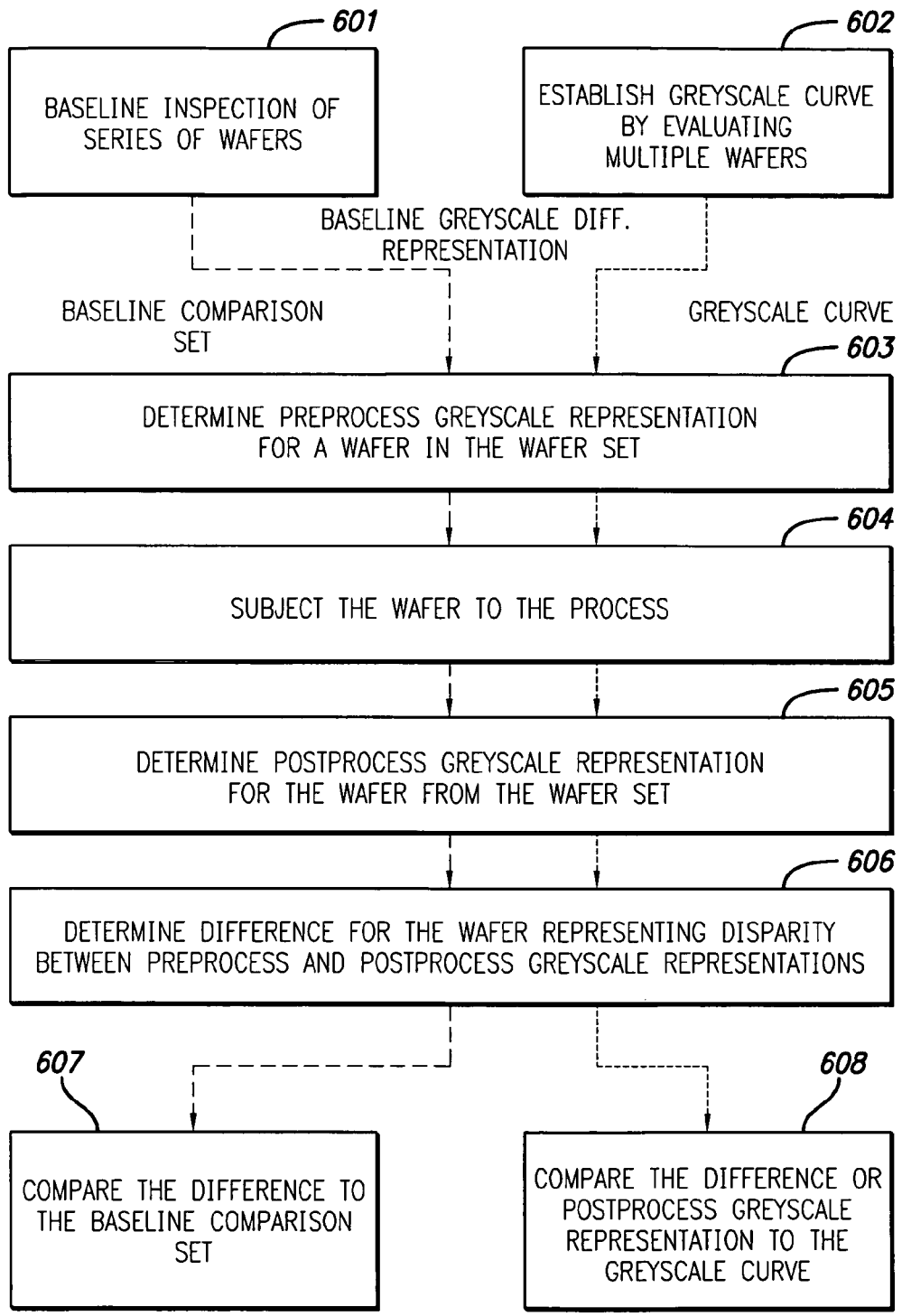
FIG. 4 is a block diagram of the current invention.

A flowchart of operation of one aspect of the system is presented in FIG. 4. The system establishes a baseline comparison set by inspecting a set of wafers before and after processing when the processing yielded minimal or acceptable errors at point 601. Alternately, as shown at point 602, the system can establish a greyscale curve by evaluating multiple wafers during various processing points and provide a curve of expected greyscale values corresponding to points during the process, such as the greyscale level expected after process one, the greyscale level expected after process two, and so on. The greyscale curve may be divided by specific processes, or alternately by elapsed time and related greyscale expected during a particular process. Thus a baseline comparison representation is generated at points 601 or 602.

From points 601 and 602, the system at point 603 determines a preprocess greyscale representation for one wafer in the semiconductor wafer set. The semiconductor wafer set includes all wafers to be inspected and evaluated, and may include one, two, or any combination, including all, wafers in a selected group of wafers. At point 604, the system subjects the one wafer in the semiconductor wafer set to the process, where the process may be any known process, including but not limited to ion implant, oxidation, CVD (chemical vapor deposition), and etching. From this point, the system at point 605 determines a postprocess greyscale representation of the one wafer in the semiconductor wafer set. The system then determines a difference for the one wafer in the semiconductor set, wherein the difference represents any disparity between preprocess and postprocess greyscale representations of the one wafer in the semiconductor set at point 606. At point 607, the system compares the resultant difference to the baseline greyscale difference representation, where the baseline greyscale difference representation is the baseline comparison set determined at point 601 by inspecting the baseline set of wafers before and after processing. At point 608, the system compares the resultant difference to the baseline greyscale difference representation, where the baseline greyscale difference representation is the greyscale curve generated at point 602 by evaluating multiple wafers during various processing points, the curve representing expected greyscale values corresponding to points during the process when the processing yielded minimal or acceptable errors. Alternately, at point 608, the system may compare the postprocess greyscale representation to the greyscale curve from point 602 to determine the percentage completion or other performance measure of the processed wafer. From this point, evaluation may occur, or further processing may take place and additional greyscale representations evaluated depending on the circumstances. For example, if a wafer or series of wafers is acceptable during one process, the postprocess representation determined at point 605 may be a preprocess representation before the wafer is subjected to the second process. Thus the foregoing may be repeated several times for different wafers, including different wafers in the wafer set. The dotted lines in FIG. 4 indicate that either one or both of the paths may be employed in the system, namely either determining a preprocess and postprocess greyscale visual representation of a wafer subjected to the process under relatively ideal conditions, and/or development of a greyscale curve. In certain circumstances, both aspects may reside on the same device, and both paths may be employed in evaluating a single wafer.

Operation of the system is as follows. Prior to processing, it is desirable to establish a baseline pre- and post-processing greyscale comparison, wherein a successful process yields a satisfactory before processing greyscale representation of a wafer and a satisfactory after processing greyscale representation of the wafer. This set of scans constitutes a baseline comparison or calibration comparison that can be scanned in the entirety and compared. In other words, the entire greyscale representation of the pre-processed wafer is assigned a greyscale value, such as a value between 1 and X, where X may take any quantity including but not limited to 256, and the entire greyscale representation of the post-processed wafer is assigned a greyscale value in the same range, such as a value between 1 and X, where X may take any quantity including but not limited to 256. The two greyscale values are subtracted, and the resultant difference and the pre- and post-processing greyscale values can be saved to a database, including a reference to the type of process performed. Any one or a combination of the difference, the pre processing greyscale value, and the post processing greyscale value may be retained as a baseline comparison set.

As noted above, an alternate method is to generate a greyscale representation that comprises a greyscale curve, wherein different points on the curve represent different times or stages in the fabrication of the completed wafer, and the curve includes greyscale values expected at certain elapsed times or at elapsed stages of the fabrication. Generation of the greyscale curve requires generating greyscale points at these times for a successful processing of a wafer, and may be created through examination of multiple inspections of multiple wafers or any other reasonable procedure available to those skilled in the art. The curve is later employed to determine how far along the subject wafer is in the process, and whether it has been over processed, under processed, or whether the process is operating incorrectly.

Once the baseline greyscale difference representation has been established, either by before-and-after processing visual representations and/or associated greyscale numerical values, or by developing the greyscale curve, the system can inspect pre-processed and post-processed subject wafers. The system inspects the entire semiconductor wafer before a specific process, such as ion implanting. The inspection includes a gray scale value collection of all of the pixels over the entire surface of the wafer. This may be done for any single wafer or group of wafers, including performing a scan on a first wafer and a last wafer to be processed at a later time. Each and every wafer in the lot may then be processed, in this example subjected to ion implanting. After processing, the wafers are again loaded individually into the system and the same wafer or wafers are inspected as had been inspected prior to processing, and the system collects grey scale values for the specific processed wafers. For example, if only one wafer was inspected before processing, the same is inspected after processing. Similarly, if the first and last wafers processed were inspected before processing, those two are inspected after processing and grey scale values collected. More or fewer may be inspected before and after processing. The system, typically using a processor or computing device, then compares the pre- and post-process grey scale values against one another for each wafer in the selected group. The system may then compare the result of the pre- and post-processed greyscale representations against the baseline comparison set. An acceptable boundary range, known as a difference boundary range, may be established, and a value outside this difference boundary range may be considered unacceptable. Additionally, boundaries for pre and post processed wafers may be established independent of one another and independent of the difference boundary range.

As an example, a system may operate with a 256 bit greyscale range, with 0 representing black and 255 representing white. The process evaluated may be ion implant, and a pre-processing greyscale value may be 128 for all pixels over the entire pre-processed wafer. A post-processing greyscale value may be 108, such that the difference therebetween is 20. Based on this, a value of 5 may be considered the boundary range, such that a value greater than 25 or less than 15 would be considered unacceptable. A boundary range of 10 for the pre-processed and 12 for the post-processed wafer, for example, may be established such that preprocessed greyscale values greater than 138 or less than 118 would be flagged, while post-processed values greater than 120 or less than 96 would be flagged. Depending on circumstances, these values may be employed for further investigation. For example, if the difference found is within acceptable boundaries, for example a difference value of 24 in the foregoing example, the system may nevertheless flag the wafer if either or both of the pre- or post-processed representations are outside their respective ranges. In this example, if the difference is 24, and the pre-processed value is 119 (within acceptable range for this example) but the post processed value is 95 (outside the acceptable range), the wafer may nevertheless be considered for subsequent inspection and/or flagged as bad.

If the first and last wafers in the process have been inspected pre-processing, they are also inspected post-processing, the greyscale difference for each wafer computed, and these differences each compared against the baseline comparison set, including possible comparison of the pre- and post-processing greyscale values. If the difference in the greyscale values is within range, the process is assessed to have been completed properly. If the difference is outside the accepted range, the process is considered incomplete or overdone. Overdone is generally considered an over application of a process, such as double implanting in an ion implantation situation.

While the invention has been described in connection with specific aspects thereof, it will be understood that the invention is capable of further modifications. This application is intended to cover any variations, uses or adaptations of the invention following, in general, the principles of the invention, and including such departures from the present disclosure as come within known and customary practice within the art to which the invention pertains.

What is claimed is:

1. A method for inspecting a semiconductor wafer set, comprising:

initially determining a baseline greyscale difference representation for at least one baseline semiconductor wafer subjected to a process, wherein the baseline greyscale difference representation represents a difference between a baseline preprocess greyscale representation and a baseline postprocess greyscale representation;

determining a preprocess greyscale representation for one wafer in the semiconductor wafer set;

subjecting the one wafer in the semiconductor wafer set to the process;

determining a postprocess greyscale representation of the one wafer in the semiconductor wafer set;

determining a difference for the one wafer in the semiconductor set, wherein the difference represents any disparity between preprocess and post process greyscale representations of the one wafer in the semiconductor set; and comparing the difference to the baseline greyscale difference representation.

2. The method of claim 1, further comprising:

determining an additional preprocess greyscale representation for an additional wafer in the semiconductor wafer set subsequent to said determining of the preprocess greyscale representation;

subjecting the additional wafer in the semiconductor wafer set to the process subsequent to said subjecting the wafer in the semiconductor wafer set to the process;

determining an additional postprocess greyscale representation of the additional wafer in the semiconductor wafer set subsequent to said determining the postprocess greyscale representation;

determining an additional difference for the additional wafer in the semiconductor set subsequent to said determining the difference for the additional wafer, wherein the additional difference represents any disparity between preprocess and post process greyscale representations of the additional one wafer in the semiconductor set; and comparing the additional difference to the baseline greyscale difference representation.

3. The method of claim 2, wherein the one wafer comprises a first wafer to be exposed to the process, and the additional wafer comprises a last wafer to be exposed to the process.

4. The method of claim 1, wherein:

said preprocess greyscale representation comprises a preprocess numeric value;

said postprocess greyscale representation comprises a postprocess numeric value; and said difference determining comprises determining a magnitude of the difference between the preprocess numeric value and the postprocess numeric value.

5. The method of claim 4, wherein:

the baseline preprocess greyscale representation comprises a baseline preprocess numeric value;

the baseline postprocess greyscale representation comprises a baseline postprocess numeric value; and the baseline greyscale difference representation represents a magnitude of the difference between the baseline preprocess numeric value and the baseline postprocess numeric value.

6. The method of claim 1, wherein determining the preprocess greyscale representation for the one wafer comprises inspecting the wafer and assigning a preprocess greyscale value representing greyscale level for all pixels in the preprocess greyscale representation.

7. The method of claim 6, wherein determining the postprocess greyscale representation for the one wafer comprises inspecting the wafer and assigning a postprocess greyscale value representing greyscale level for all pixels in the postprocess greyscale representation.

8. The method of claim 1, further comprising:

evaluating the comparison between the difference to the baseline representation, and if outside a predetermined threshold, investigating the one wafer for specific defects.

9. The method of claim 1, further comprising:

evaluating the comparison between the difference to the baseline representation, and if outside a predetermined threshold, considering the one wafer defective.

10. The method of claim 1, further comprising:

determining a subsequent preprocess greyscale representation for the one wafer in the semiconductor wafer set;

subjecting the one wafer in the semiconductor wafer set to a second process;

determining a subsequent postprocess greyscale representation of the one wafer in the semiconductor wafer set; and determining a difference for the one wafer in the semiconductor set, wherein the difference represents any disparity between subsequent preprocess and subsequent post process greyscale representations of the one wafer in the semiconductor set.

11. The method of claim 10, wherein the subsequent preprocess greyscale representation is similar to the postprocess greyscale representation.

12. A method for inspecting a wafer, comprising:

initially determining a baseline greyscale difference representation for at least one baseline semiconductor wafer subjected to a process;

determining a preprocess greyscale representation for the wafer subsequent to said initially determining the baseline greyscale difference representation;

subjecting the wafer to the process;

determining a postprocess greyscale representation for the wafer;

determining a difference for the wafer, wherein the difference represents any disparity between preprocess and postprocess greyscale representations of the wafer; and comparing the wafer difference to the baseline greyscale difference representation.

13. The method of claim 12, wherein the at least one baseline semiconductor wafer has been exposed to the process.

14. The method of claim 13, wherein the baseline greyscale difference representation represents a difference between a baseline preprocess greyscale representation and a baseline postprocess greyscale representation of the baseline semiconductor wafer.

15. The method of claim 14, wherein:

the baseline preprocess greyscale representation comprises a baseline preprocess numeric value;

the baseline postprocess greyscale representation comprises a baseline postprocess numeric value; and the baseline greyscale difference representation represents a magnitude between the baseline preprocess numeric value and the baseline postprocess numeric value.

16. The method of claim 13, wherein comparing the wafer difference to the baseline greyscale difference representation occurs subsequent to determining the wafer difference.

17. The method of claim 12, wherein:

said preprocess greyscale representation comprises a preprocess numeric value;

said postprocess greyscale representation comprises a postprocess numeric value; and said wafer difference determining comprises determining a magnitude of the difference between the preprocess numeric value and the postprocess numeric value.

18. The method of claim 12, wherein determining the preprocess greyscale representation for the one wafer comprises inspecting the wafer and assigning a preprocess greyscale value representing greyscale level for all pixels in the preprocess greyscale representation.

19. The method of claim 12, further comprising:
evaluating the comparison between the wafer difference to the baseline representation, and if outside a predetermined threshold, investigating the wafer for specific defects.

20. The method of claim 12, further comprising:
evaluating the comparison between the wafer difference to the baseline representation, and if outside a predetermined threshold, considering the wafer defective.

21. The method of claim 12, further comprising:
determining a subsequent preprocess greyscale representation for the wafer;
subjecting the wafer to a second process;
determining a subsequent postprocess greyscale representation of the wafer; and
determining a difference for the wafer, wherein the difference represents any disparity between subsequent preprocess and subsequent post process greyscale representations of the wafer.

22. A method for inspecting a specimen, comprising:
initially determining a baseline greyscale difference representation for at least one baseline semiconductor wafer subjected to a process;
computing a preprocess numeric greyscale value representing a preprocess greyscale representation of the specimen subsequent to said initially determining the baseline greyscale difference representation;
subjecting the specimen to the process;
computing a postprocess numeric greyscale value representing a postprocess greyscale representation of the specimen;
comparing the preprocess numeric greyscale value to the postprocess numeric greyscale value to determine a specimen difference; and
comparing the specimen difference to the baseline grayscale difference representation representing baseline grayscale difference for at least one baseline specimen.

23. The method of claim 22, wherein the at least one baseline specimen is subjected to the process prior to determining the preprocess greyscale representation for the specimen.

24. The method of claim 23, wherein the baseline greyscale difference representation represents a difference between a baseline preprocess greyscale representation and a baseline postprocess greyscale representation of the baseline specimen.

25. The method of claim 24, wherein said comparing comprises determining a magnitude between preprocess and postprocess numeric representations of the specimen.

* * * * *